US00PP10490P

United States Patent [19]

Friday

[11] Patent Number: Plant 10,490

[45] Date of Patent: Jul. 14, 1998

[54] 'P.F. 7' PEACH TREE

[75] Inventor: Paul Jan Friday, Coloma, Mich.

[73] Assignee: Paul J. Friday, Coloma, Mich.

[21] Appl. No.: 770,124

[22] Filed: Dec. 19, 1996

[51] Int. Cl.[6] ..... A01H 5/00

[52] U.S. Cl. ..... Plt./43.1

[58] Field of Search ..... Plt./43.1

[56] References Cited

U.S. PATENT DOCUMENTS

P.P. 6,759 4/1989 Doyle ..... Plt./43.1

P.P. 9,548 5/1996 Kovacerich ..... Plt./43.1

*Primary Examiner*—James R. Feyrer

[57] ABSTRACT

A new and distinct variety of peach tree having the following unique combination of desirable features:

1. The new and distinct variety of peach tree is of moderate upright growth and a regular and productive bearer of large peaches having a diameter of between about 2½" to 3".
2. Producing a very firm fruit having a resilient flesh texture.
3. Blossoms are partially showy when in full bloom.
4. A substantially spherical fruit with skin of lavender-red color overlying a light to whitish yellow at maturity.
5. Early season maturing fruit of good taste.
6. An early season maturing fruit of good storage and shelf life.

1 Drawing Sheet

ORIGIN OF VARIETY

The new peach tree (hereinafter referred to as the P.F. 7 peach tree, *Prunus persica*) was originated by Paul Friday in the experimental orchard, which is maintained for the purpose of breeding peach trees, at Paul Friday Farms Inc., located in Coloma, Mich. Coloma is located in the southwest section of Michigan.

In an ongoing mass selection breeding program, superior seedlings of unrecorded parentage are maintained as seed sources for the production of seeds which are collected and planted in mass. The seed producing parent trees are maintained solely as proprietary trees fro breeding purposes and have not been released from the experimental orchard, where such trees can be evaluated for their adaptability to local and regional growing conditions. Seeds resulting from open pollination of the trees in the experimental orchard are regularly planted in mass to produce new populations of seedlings which are cultured and monitored to maturity. Trees with superior attributes are retained for further observation and testing, and contribute seeds to advancing generations of new populations of seedlings.

The tree of this application, P.F. 7, was cultivated selection from one such a seedling population, and was based on the numerous superior genetic attributes of this tree which are described in the botanical descriptions to follow.

ASEXUAL REPRODUCTION OF THE VARIETY

The new and distinct variety of peach tree was asexually propagated by budding as performed in the experimental orchard of Paul Friday Farms, Inc., located in Coloma, Mich. The asexual propagation demonstrates that such repdoduction of the characteristics of the tree are consistent and are established and transmitted through succeding propagation.

SUMMARY OF THE VARIETY

The new and distinct variety of peach tree is of moderate upright growth and a regular and productive bearer of peaches. The blossoms are characterized by being contracted or partially spread when in full bloom. At the same time the petals of the blossoms are of lesser length than the length of petals of the normal showy blossom as exemplified by the Loring peach blossom.

The blossoms of the present peach tree at full bloom may be characterized as being partially non-showy.

The fruit at maturity is large, having flesh of very clear yellow.

The skin is smooth having moderate down and is of slightly orange to orange-red color overlying light or whitish yellow. At maturity the peach is a true spherical having an average diameter ranging between about 2½" to 3".

The fruit has a firm flesh and may be described as resilient to the extent that the flesh is yieldable and restorable to its original state when subjected to impact forces which may cause permanent deformities in peaches of the commercial varieties. The firmness of the fruit facilitates handling and packaging of the peaches without damaging the same for shipment. This results in less spoilage and also increases the shelf life.

The fruit matures in the early part of the peach growing season of southwestern Michigan. The fruit is a semi-cling type and as mentioned heretofore is of orange to orang-red color overlying light or whitish yellow and has a very attractive appearance.

BRIEF DESCRIPTION OF THE DRAWINGS

In the accompanying drawing, the top photograph depicts the terminal portion of the typical branch of this tree taken at about the time of fruit maturity, showing the exceptional size of the leaves, the internode length, and the characteristics of the bark of the current season's growth. The bottom photograph shows one whole fruit positioned to show the blossom end of the fruit, the very inconspicuous suture, and the very small pistil point. Also, depicted are three sectioned fruit specimens with varying portions of the fruit flesh removed to illustrate the solid yellow coloration of the flesh of the fruit from the skin to the stone. The uniform size and shape of the fruit is shown as is the uniform exterior blushed color of the skin of the fruit produced by this tree. The illustrations were taken shortly after being picked at a maturity stage of firm ripe. The colors are as nearly true as is reasonably possible in a photographic color representation of this type.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Panatone Matching System (PMS) as used internationally to identify printed colors.

Tree;

*Height.*—Unpruned 15'.
*Width.*—Unpruned 15'.
*Size.*—Medium-large.
*Vigor.*—Medium vigor, 2' to 5' per year.
*Density.*—Medium, pruning requirement heavy.
*Form.*—With routine pruning this variety makes a large spacious vase-shaped tree with very strong right-angle branching.
*Production.*—This variety is productive, requiring approximately one-half of the fruit to be removed to achieve optimum size. Second generation trees withstood winter temperatures in 1994 of 18 degrees Fahrenheit below zero without causing much damage to the trees.
*Bearer.*—Consistent.
*Disease resistance to bacterial leaf and fruit spot.*—Very good.

Trunk:

*Size.*—Medium.
*Surface.*—Smooth to medium shaggy.

Branches:

*Size.*—Medium.
*Surface.*—Smooth to medium.
*Internode length.*—standard size, normally at start of season and small at the end.
*Lenticels.*—Large number and medium size.
*Color.*—Gray.

Leaves:

*Size.*—Large. Average length — 7". Average width — 2".
*Form.*—Lanceolate — pointed.
*Stipules formation.*—Unobserved at this time.
*Thickness.*—Medium.
*Texture.*—Medium.
*Margin.*—Serrate.
*Petiole.*—Medium length — medium thickness not a discerning characteristic.
*Gland.*—Very small and insignificant — number varies from 0 to 2. Average 1. Located on base of leaf and upper portion of petiole. The shape is reniform and color of the leaf glands is eggshell white.

Flower buds:

*Size.*—Medium.
*Length.*—Medium.

Flowers:

*Blooming period.*—Apr. 7, 1996 to Apr. 14, 1996.
*Size.*—Medium or partially showy inclined upright petal pattern (about 13/16 inch diameter).
*Pollen.*—Present, self-fertilizing.
*Color.*—Pink.

Fruit:

*Maturity when described.*—Firm ripe.
*Date of first picking.*Jul. 25, 1996. (About 12 days before picking Redhaven. Fruit matures very evenly and can be harvested in two pickings).
*Date of last picking.*—Jul. 31, 1996.
*Size.*—Average — 2½" in diameter.
*Form.*—True spherical shape.
*Suture.*—Very shallow.

Skin:

*Thickness.*—Medium.
*Texture.*—Tough, tenacious to skin.
*Tendency to crack.*—None.
*Down.*—Moderate to little.
*Color.*—Yellow ground color (155). Nearly overspread (80%) with red (157).

Flesh:

*Texture.*—Firm the fruit of this tree can be held on the tree until reaching the "soft ripe" stage of ripeness without any dropping, clearly an advantage in "pick your own" orchard operations. The flesh of this fruit is somewhat fibrous.
*Ripens.*—Relatively even.
*Flavor.*—Good, a balance between sweet and acid.
*Aroma.*—Pleasant.
*Eating quality.*—Excellent and very juicy.
*Color.*—Yellow (114). Pit cavity also yellow (114).

Stone:

*Type.*—Semi cling.
*Size.*—Average length — 1½". Average width — 1". Average thickness — ½".
*Form.*—Ovid.
*Base.*—Straight.
*Apex.*—Pointed.
*Sides.*—Nearly equal.
*Surface.*—Irregularly furrowed.
*Color.*—Light tan (120).
*Tendency to crack.*—None.

Use: Desert.
Shipping quality: Excellent.
Keeping quality: Good.

The tree and its fruit herein described may vary in slight detail as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as illustrated and described as a large size tree, vigorous in growth and a regular and productive bearer of large size, yellow flesh semi-cling fruit with good flavor and eating quality; and a fruit of substantially spherical shape having a firm flesh, and a red skin color covering over 80% of the fruit at maturity which occurs about 12 days before maturity of the 'Redhaven' peach variety; and, this tree has a remarkable ability to produce practically all fruit void of split pits or skin blemishes; extraordinary for an early peach. This tree has a particularly wide leaf.

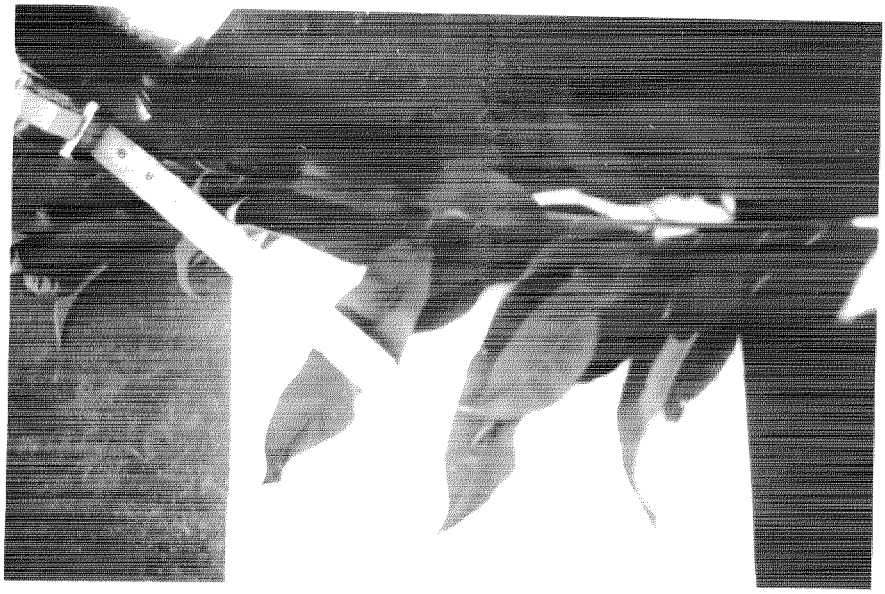
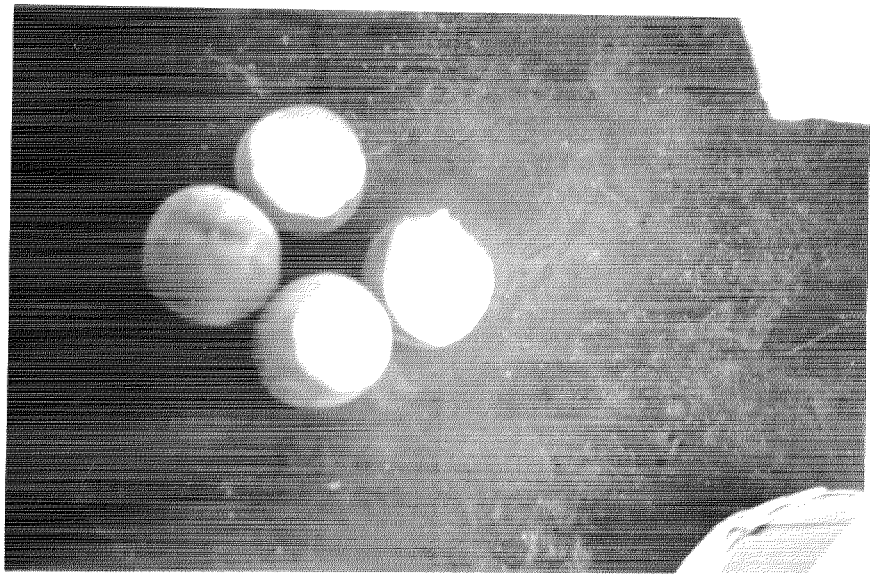

* * * * *